United States Patent [19]
Aoki

[11] Patent Number: 5,656,190
[45] Date of Patent: Aug. 12, 1997

[54] CONTROLLER FOR A HEATER FOR AN AIR-FUEL RATIO SENSOR AND A METHOD THEREOF

[75] Inventor: Keiichiro Aoki, Susono, Japan

[73] Assignee: Toyota Jidosha Kabushiki Kaisha, Aichi, Japan

[21] Appl. No.: 601,392

[22] Filed: Feb. 14, 1996

[30] Foreign Application Priority Data

Feb. 20, 1995 [JP] Japan .................................. 7-030617

[51] Int. Cl.$^6$ ...................................................... H05B 1/02
[52] U.S. Cl. ........................... 219/505; 219/497; 219/501; 374/164
[58] Field of Search ...................................... 219/505, 504, 219/497, 499, 501; 374/163, 164

[56] References Cited

U.S. PATENT DOCUMENTS

| | | | |
|---|---|---|---|
| 4,300,037 | 11/1981 | Padden | 219/497 |
| 4,740,671 | 4/1988 | Kuroda et al. | 219/497 |
| 4,897,527 | 1/1990 | Cripps et al. | 219/492 |
| 5,216,743 | 6/1993 | Seitz | 392/490 |

FOREIGN PATENT DOCUMENTS 1158335  6/1989  Japan .
3223664  10/1991  Japan .

*Primary Examiner*—Mark H. Paschall
*Attorney, Agent, or Firm*—Kenyon & Kenyon

[57] ABSTRACT

The object of the present invention is to provide a controller for a heater for an air-fuel ratio sensor, and a method thereof, which activates the sensor element at an early stage so as to start the air-fuel ratio feedback control to clean the exhaust gas from the engine as early as possible, and avoids deterioration of the heater and the sensor element due to overheating thereof.

The controller has a power supplying device for supplying electric power to a heater for heating an air-fuel ratio sensor arranged in an exhaust system of an internal combustion engine to maintain the air-fuel ratio sensor activated and has a resistance measuring device for measuring the resistance of the heater. The controller also has a power supply controlling device for controlling the power supply to the heater supplied by the power supplying device such that the resistance of the heater measured by the resistance measuring device is kept under a first upper limit when activating the air-fuel ratio sensor, and is kept under a second upper limit that is lower than the first upper limit after the air-fuel ratio sensor has been activated, thereby avoiding deterioration of the heater and the air-fuel ratio sensor.

2 Claims, 7 Drawing Sheets

CONTROLLER FOR A HEATER FOR AN AIR-FUEL RATIO SENSOR AND A METHOD THEREOF

FIELD OF THE INVENTION

The present invention relates to a controller for a heater for an air-fuel ratio sensor and a method thereof and, more particularly, to a controller which has a power supply means for supplying electric power to the heater provided in the air-fuel ratio sensor arranged in an exhaust gas system of an engine to maintain the air-fuel ratio sensor activated and which has a resistance measuring means for measuring the resistance of the heater.

BACKGROUND INFORMATION

An air-fuel ratio sensor which uses zirconia solid electrolyte as a sensor element is known. The sensor element detects current that changes in response to the concentration of oxygen in an exhaust gas. This air-fuel ratio sensor does not operate if the temperature of the sensor element is not maintained at approximately 650° C. to 750° C. Therefore, the air-fuel ratio sensor has a heater, which, for example, has platinum electrodes, to maintain the temperature of the sensor element at 650° C. to 750° C. In the air-fuel ratio sensor having a heater, the temperature of the sensor element can be increased by supplying a higher electric power to the heater. If the electric power supply to the heater is controlled, the temperature of the sensor element can be controlled.

As the air-fuel ratio sensor is arranged in an exhaust pipe, the air-fuel ratio sensor is heated not only by the heater but also by the exhaust gas and radiant heat from the engine body including the exhaust pipe. Therefore, the temperature of the sensor element is influenced not only by the temperature of the heater but also by the exhaust gas and the engine body. Accordingly, in a light load engine condition, in which the temperatures of both exhaust gas and the engine body are low, the electric power supply to the heater must be increased to maintain the temperature of the sensor element at 650° C. to 750° C. On the other hand, in a heavy load engine condition in which the temperatures of both exhaust gas and the engine body are high, the electric power supply to the heater must be decreased to maintain the temperature. The electric power supply to the heater necessary for maintaining the temperature of the sensor element at 650° C. to 750° C., is empirically measured depending on engine operating conditions, and the measured data are memorized as basic electric power supply data. Then, the temperature of the sensor element is controlled to 650° C. to 750° C., by heating the heater in accordance with the basic electric power supply depending on the engine operating conditions.

The heater having the platinum electrodes, on the other hand, is deteriorated when it is kept for a long time at high temperature, for example, at 1120° C. or more. Therefore, the basic power supply is controlled so that the heater temperature does not exceed 1100° C. At the engine start up time, it is necessary to maintain the temperature of the heater as high as possible. At this time, however, it is necessary to increase the temperature of the sensor element to 650° to 750° C. as quickly as possible. Therefore, the basic power supply is determined so that the temperature of the heater reaches 1100° C. at the engine start up time. Furthermore, it is also necessary to maintain the temperature of the heater in the light load engine condition.

As explained above, the basic power supply is set to low at the heavy load engine condition, and set to high at the light load engine condition, so that the power supply is rapidly increased when the engine condition is changed from the heavy load to the light load. However, for a period of time after changing the engine condition from heavy load to light load, the temperature of the sensor element is maintained at a high level by the radiant heat from the engine body since the temperature of the engine body is kept high. Therefore, the temperature of the heater is kept over 1120° C. for a long time after the engine condition is changed from heavy load to light load because the power supply rapidly increases in response to the change in engine condition form heavy load to light load. This results in damage to the heater and the sensor element.

The electrical resistance is proportional to the temperature of the heater. Therefore, the temperature of the heater can be determined from the resistance. To solve the above mentioned problem, Japanese Unexamined Patent Publication No. 1-158335 has proposed a heater controller that measures the resistance of the heater and reduces the basic power supply for a period after the engine condition is changed from heavy load to light load and when the resistance of the heater exceeds the limit resistance of the heater at, for example, 1100° C.

However, according to the heater controller disclosed in Japanese Unexamined Patent Publication No. 1-158335, the power supply to the heater is reduced when the engine condition is changed from heavy load to light load before the engine is fully warmed up or when the resistance of the heater is mismeasured as the resistance of the heater exceeds the limit resistance, which results in decreasing the temperature of the air-fuel ratio sensor to an inactivated state thereof. Once the temperature of the sensor element is reduced, the air-fuel ratio feedback control cannot be used until the air-fuel ratio sensor is reactivated. This results in a failure to clean the exhaust gas. To solve this problem, Japanese Unexamined Patent Publication No. 3-223664 has proposed a heater controller that sets a predetermined period after the engine condition is changed from heavy load to light load depending on the engine warm up condition. The period under the condition when the engine is not yet warmed up, is set shorter than the period when the engine is warmed up. Thus, the basic power supply can be set relatively high. However, the heater controller disclosed in Japanese Unexamined Patent Publication No. 3-223664 records the limit resistance of the heater under the light load engine condition. Therefore, this heater controller cannot supply more electric power, to the heater, than the recorded value, at the engine start up time when the current resistance is lower than the upper limit resistance of the heater because the basic power supply is set such that the resistance of the heater may not exceed the upper limit resistance which was obtained when it was recorded, as explained before. As a result, it takes a long time to heat the air-fuel ratio sensor until it is activated.

Furthermore, the heater controller above prevents the heater and the sensor element from deteriorating by setting the limit resistance as an upper limit of the heater. On the other hand, the heater and the sensor element are at high temperature when the engine condition is changed from heavy load to light load after the engine is warmed up. At this time, if the basic power supply is supplied to heat the heater in accordance with the light load engine condition up to the upper limit, the heater is further warmed up by the exhaust gas and radiant heat from the engine body. As a result, the heater and the sensor element are overheated and are deteriorated. Therefore, the upper limit has to be set low. On the contrary, the air-fuel ratio feedback control of the engine must be started as early as possible after the engine start up to clean the exhaust gas. For this reason, the sensor element has to be activated as early as possible. Therefore, the upper limit has to be set high. These requirements contradict one another.

SUMMARY OF THE INVENTION

The object of the present invention to provide a controller for a heater of an air-fuel ratio sensor, and a method thereof, which eliminates the aforementioned problems, activates the sensor element at the early stage so as to start the air-fuel ratio feedback control as early as possible, and avoids the deterioration of the heater and the sensor element due to overheating when the engine condition is changed from heavy load to light load after the engine is warmed up, and further improves the efficiency of the power supply to the heater.

The present invention provides a controller for a heater of an air-fuel ratio sensor, and a method to control the heater, as shown in FIG. 1. The controller according to the present invention has a power supply means A for supplying an electric power to a heater 17 for heating an air-fuel ratio sensor 15 arranged in an exhaust system of an internal combustion engine to maintain the air-fuel ratio sensor 15 activated and a resistance measuring means B for measuring a resistance of the heater 17. The controller has a power supply control means C for controlling the power supply to the heater 17 supplied by the power supply means A such that the resistance of the heater 17 measured by the resistance measuring means B is kept under a first upper limit when the air-fuel ratio sensor 15 is not activated, and is kept under a second upper limit that is lower than the first upper limit after the air-fuel ratio sensor 15 has been activated, thereby avoiding deterioration of the heater and the air-fuel ratio sensor.

A method for controlling a heater of an air-fuel ratio sensor, for avoiding deterioration of the heater and the air-fuel ratio sensor, according to the present invention, comprising the steps of:

measuring the resistance of the heater 17 provided in the air-fuel ratio sensor 15 arranged in an exhaust gas system of an engine to maintain the air-fuel ratio sensor 15 activated, controlling the power supply to the heater 17 so that the measured resistance is kept under a first upper limit when activating the air-fuel ratio sensor 15, and controlling the power supply to the heater 17 so that the measured resistance is kept under a second upper limit that is lower than the first upper limit after the air-fuel ratio sensor 15 has been activated.

In order to accomplish the object of the present invention, FIG. 1 shows a controller that heats the heater 17 up to a high temperature so that air-fuel ratio sensor 15 is rapidly activated because the temperatures of the air-fuel ratio sensor 15 and the surroundings of the sensor are low when the air-fuel ratio sensor has not yet warmed up at the engine start up time. To accomplish this, the controller is controlled to heat the heater 17 until the resistance of the heater 17, that is proportional to the temperature thereof, reaches to a first upper limit resistance that protects the heater 17 from deterioration. On the other hand, once the air-fuel ratio sensor 15 has been warmed up, the temperature of the air-fuel ratio sensor 15 and the surroundings of the sensor are high. Therefore, the activated state of the air-fuel ratio sensor 15 can be maintained even if the heater is set at low temperature, so that the controller is controlled to heat the heater 17 such that the resistance of the heater 17 is kept under a second upper limit resistance that is lower than the first upper limit. When the engine condition is changed from the heavy load to light load after the engine is warmed up, even if the temperature of the air-fuel ratio sensor 15 and the surroundings of the sensor are increased by the exhaust gas and radiant heat from the engine body, the heater and the sensor element can be protected from deterioration due to overheating by the heater because the resistance of the heater 17 is kept under the second upper limit resistance.

BRIEF DESCRIPTION OF THE DRAWINGS

The present invention will be more clearly understood from the description as set forth below with reference to the accompanying drawings, wherein.

DESCRIPTION OF THE PREFERRED EMBODIMENTS

Figure 1:
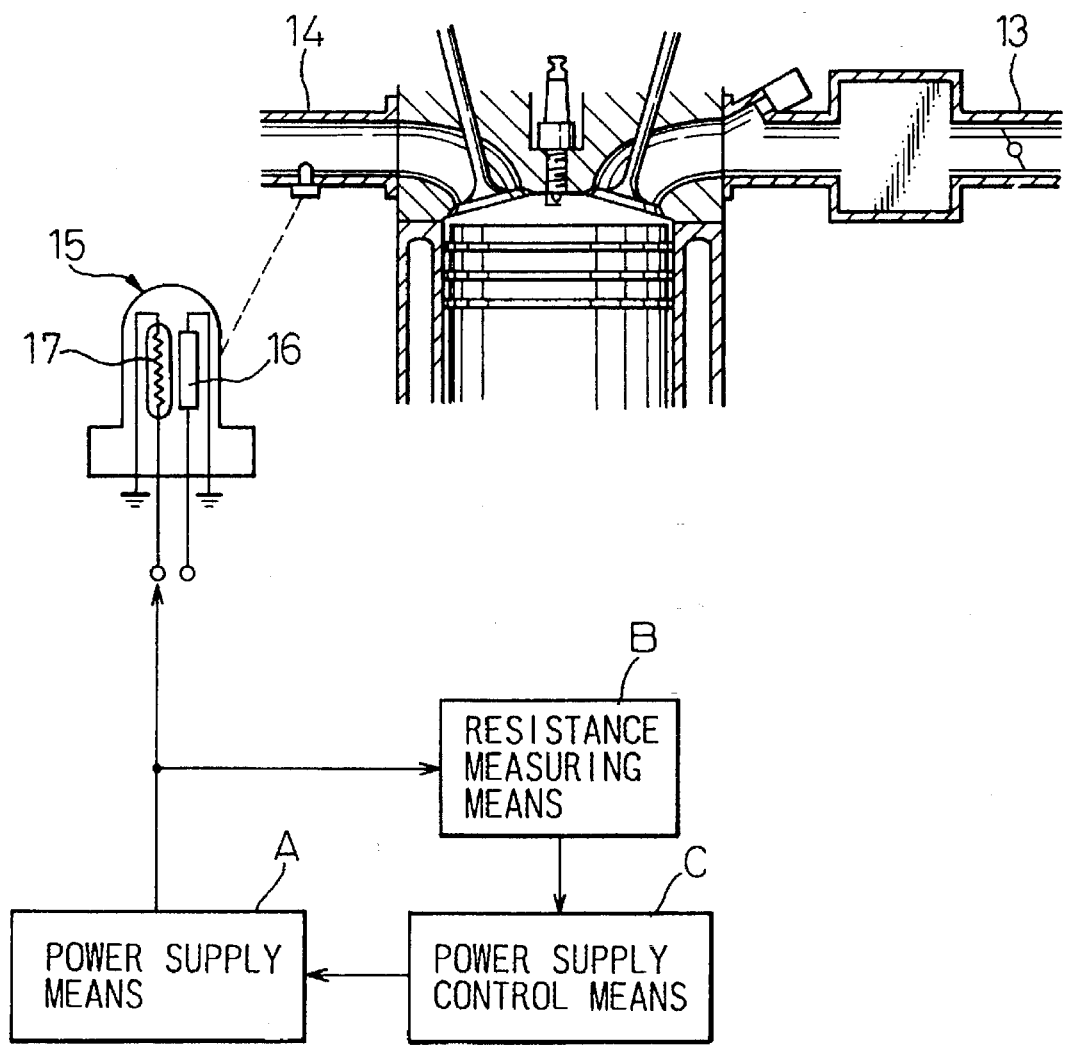
FIG. 1 is a block diagram showing a basic structure of the present invention.
Figure 2:
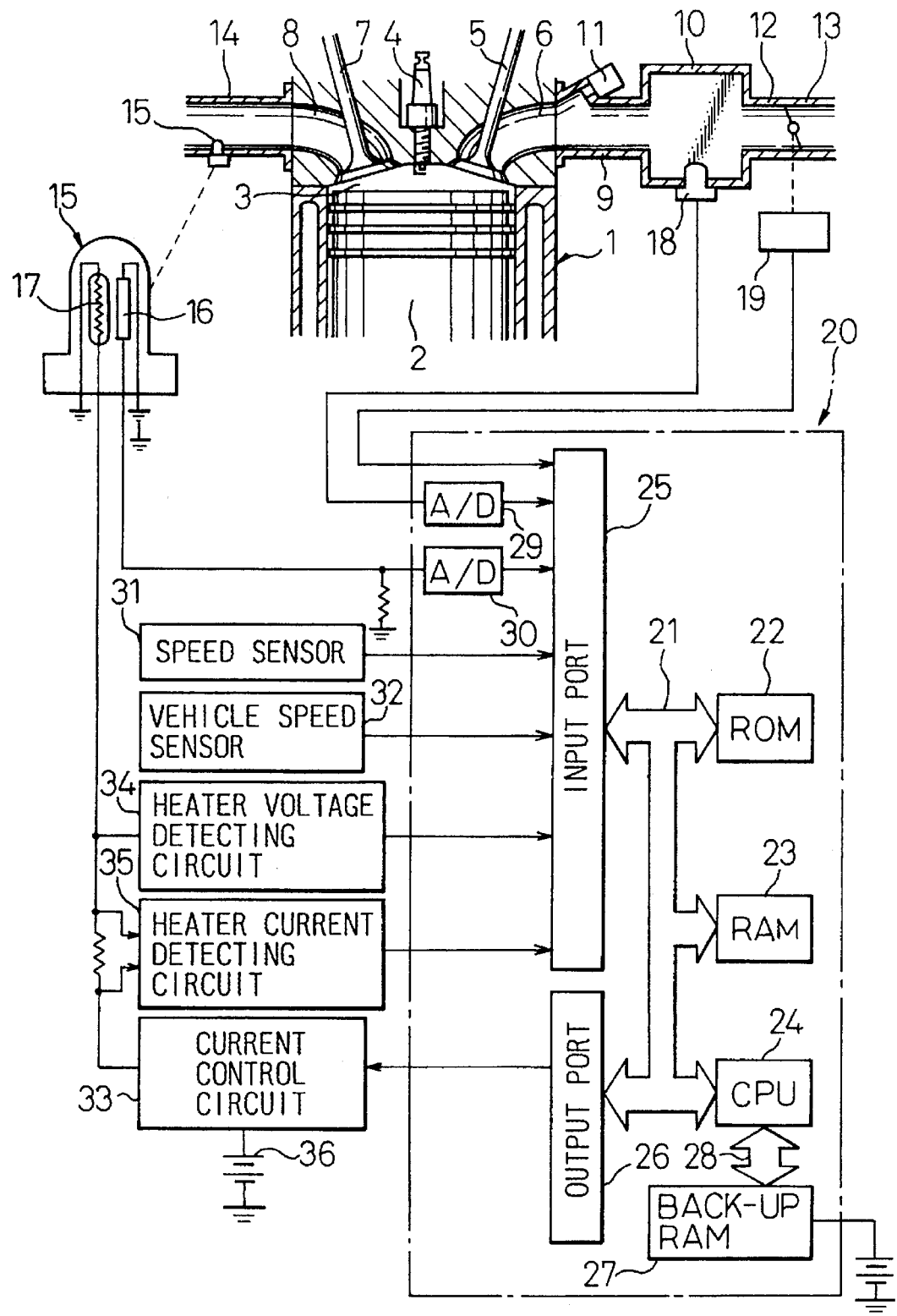
FIG. 2 is a general view showing an embodiment of a controller for a heater for an air-fuel ratio sensor according to the present invention.

FIG. 2 shows an embodiment of a controller for a heater of an air-fuel ratio sensor according to the present invention. In FIG. 2, reference number 1 denotes an engine body, 2 denotes a piston, 3 denotes a combustion chamber, 4 denotes an ignition plug, 5 denotes an intake valve, 6 denotes an intake port, 7 denotes an exhaust valve and 8 denotes an exhaust port. The intake port 6 is connected to a surge tank 10 via a branch duct 9. A fuel injector 11 is arranged in each branch duct 9 to inject fuel for each corresponding intake port 6. The ignition timing for firing the ignition plug 4, the amount of fuel injection from the injector 11 and the injecting timing are controlled by an electronic control unit 20. The surge tank 10 is connected to a cleaner (not shown) via a intake duct 12. A throttle valve 13 is arranged in the intake duct 12. The exhaust port 8 is connected to an exhaust manifold 14. The air-fuel ratio sensor 15 that detects the concentration of oxygen in the exhaust gas from the engine 1 is arranged in the exhaust manifold 14. The FIG. 2 also shows an enlarged drawing of the air-fuel ratio sensor 15.

The air-fuel ratio sensor 15 has a sensor element 16 consisting of, for example, zirconia and a heater 17 for heating the sensor element 16 arranged beside it.

The electronic control unit 20 is a digital computer having a ROM (Read Only Memory) 22, a RAM (Random Access Memory) 23, a CPU (micro processor) 24, an input port 25 and an output port 26. These elements are mutually connected to one another with a bi-directional bus 21. The CPU 24 is also connected to a back-up RAM 27 via a bus 28. In the surge tank 10, a pressure sensor 18 outputs an analog voltage proportional to a pressure PM in the surge tank 10. The output from the pressure sensor 18 is input to the input port 25 via an A/D converter 29. The throttle valve 13 is linked to a throttle switch 19 that outputs a signal indicating that the throttle valve 13 is opened at an idling position. The output from the throttle switch 19 is input to the input port 25. The sensor element 16 of the air-fuel ratio sensor 15 supplies current proportional to concentration of oxygen in the exhaust gas from the engine 1, in other words, the current is proportional to the air-fuel ratio of the exhaust gas. The sensor element 16 outputs an analog voltage signal proportional to the current. This signal is input to the input port 25 via an A/D converter 30.

Furthermore, a speed sensor 31 for detecting the engine speed that outputs a signal NE and a vehicle speed sensor 32 for detecting the vehicle speed that outputs a signal S are also connected to the input port 25. On the other hand, a current control circuit 33 for controlling the current to the heater 17 of the air-fuel ratio sensor 15 is connected to the output port 26. The current is controlled in accordance with the duty ratio signal output from the output port 26. A heater voltage detecting circuit 34 and a heater current detecting circuit 35 are provided between the heater 17 and the current control circuit 33. The heater voltage detecting circuit 34 detects the voltage between both ends of the heater 17 which is input to the input port 25. The heater current detecting circuit 35 detects the voltage representing the current passing through the heater 17 which is input to the input port 25. The electronic control unit 20 controls the heater 17 of the air-fuel ratio sensor 15 according to the present invention, as well as fuel injection control, ignition timing control, of the combustion engine, etc.

Figure 3:
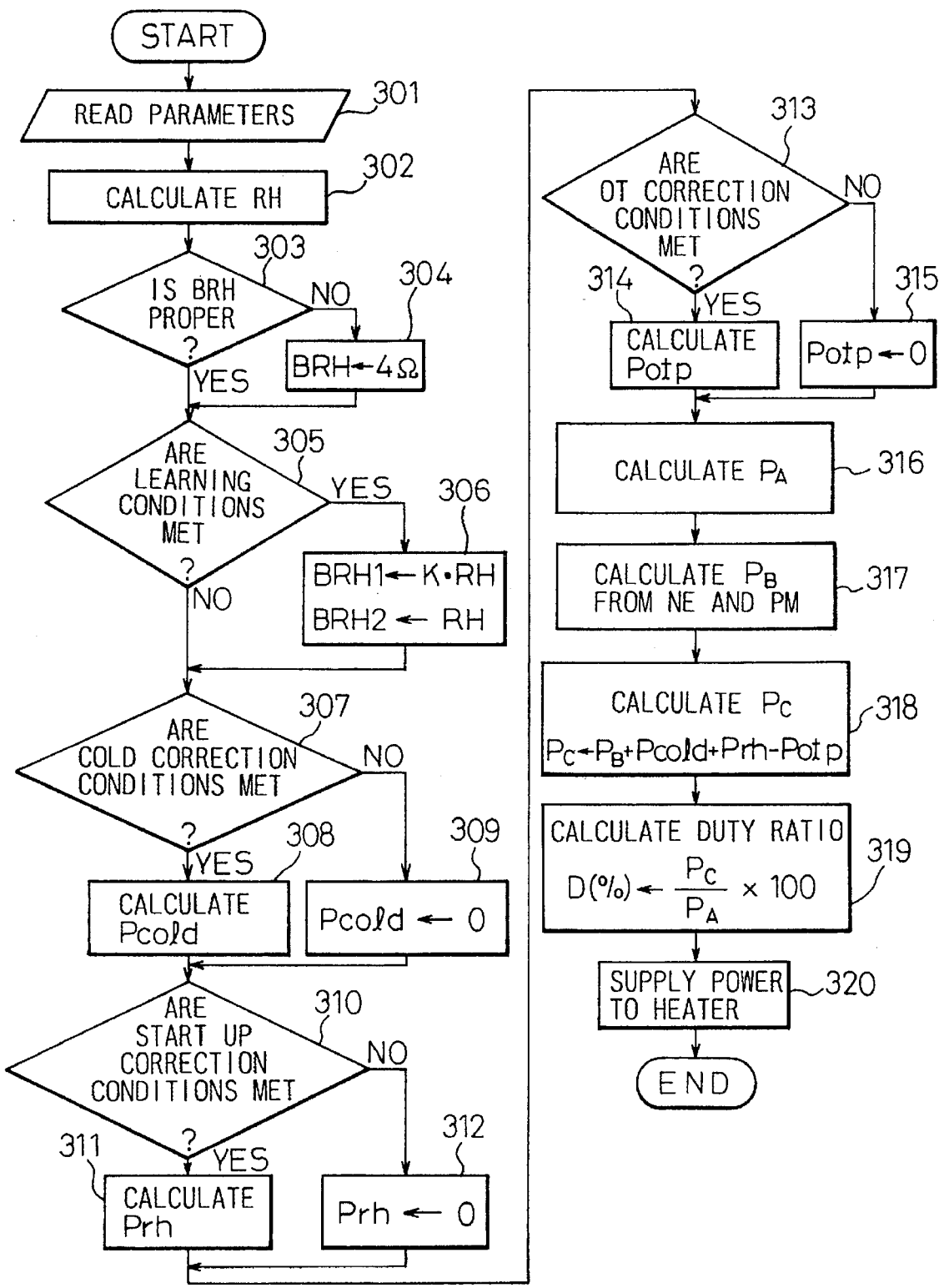
FIG. 3 is a flowchart showing a control routine for a heater for an air-fuel ratio sensor according to the present invention.

FIG. 3 is a flowchart showing a control routine for a heater 17 of an air-fuel ratio sensor 15 according to the present invention. This routine is executed by an interrupt that occurs at every predetermined time, for example, 100 msec. The current to the heater 17 is supplied from a power source 36 and is controlled in accordance with the duty ratio signal input to the current control circuit 33. The duty ratio is determined based on the engine operating conditions and whether or not the air-fuel ratio sensor 15 is activated. After the routine is started, in step 301, parameters such engine rotation NE, intake air pressure PM, heater voltage $V_h$, heater current $I_h$, etc. are read from various sensors and the detecting circuits.

Figure 4:
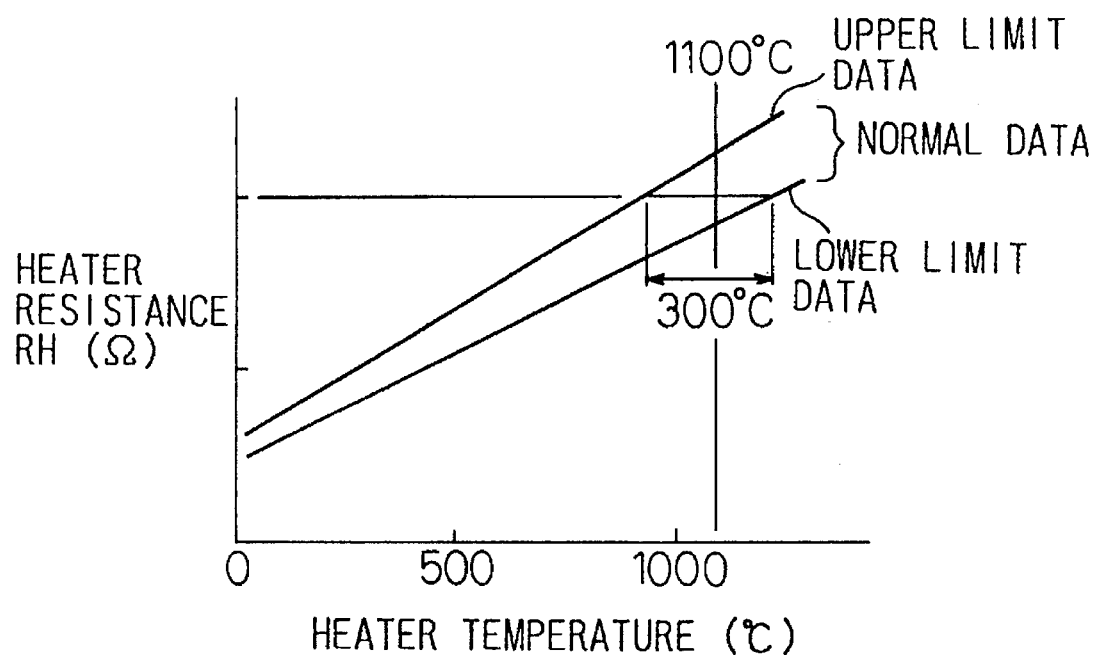
FIG. 4 is a characteristic graph showing a relationship between the temperature and the resistance of a heater.

In step 302, the heater resistance RH is calculated from the heater voltage $V_h$ and the heater current $I_h$. If platinum is used for an element of the heater 17, the relationship between the resistance and the temperature of the heater is linear as shown in FIG. 4. The slopes of the linearity are different between heaters.

In step 303, it is determined whether or not the stored values BRH (BRH1 and BRH2) associated with the resistance RH of the heater 17 currently stored in the back-up RAM 27 are proper. If the values BRH are determined as improper in step 303, the stored values BRH are set to a determined value, for example, 4Ω (step 304). If the values BRH are determined as proper in step 303, step 305 is executed. In step 303, the values 1/BRH are also used for the judgement. The values 1/BRH are also stored in the back-up RAM 27 when the values BRH are rewritten.

In step 305, it is determined whether or not conditions for learning the stored values BRH associated with the resistance RH of the heater 17 are met. If the feedback control of an air-fuel ratio has been started in accordance with the output of the sensor element 16 of the air-fuel ratio sensor 15, the intake air pressure PM is under the predetermined value, the engine speed NE is kept under predetermined value for more than a minute, and the power supply to the heater 17 is over the predetermined value, it is determined that the conditions for learning the stored values BRH are met. Namely, it is determined that the conditions for learning the stored values BRH are met when the engine operating conditions are stable and the temperature of the heater 17 is controlled to be 1100° C. The feedback control of an air-fuel ratio based on the output from the sensor element 16 of the air-fuel ratio sensor 15 is performed if all the following conditions are met. The conditions are: the engine is not in the start up time; the engine is determined as warmed up from the temperature of the coolant of the engine (the temperature equal 70° C. or more); the control for correcting the amount of fuel injection to be increased at the time after the engine is started up, or at the time of warming up the engine, bearing a heavy load or accelerating the engine, is not performed; the fuel cut control is not performed; and the air-fuel ratio sensor 15 is determined to be activated.

In step 305, it is determined whether or not the conditions for learning are met. If it is determined YES in step 305, then in step 306, a first heater limit resistance BRH1 that guards the heater resistance from deterioration during warming up the air-fuel ratio sensor 15 is calculated by multiplying the heater resistance RH obtained in step 302 by a temperature coefficient K, and a second heater limit resistance BRH2 that guards the heater resistance from deterioration after warming up the air-fuel ratio sensor 15 is calculated by setting the heater resistance RH obtained in step 302, and these data are stored in the back-up memory RAM 27. In this way, by storing these data in the back-up memory RAM 27, the data BRH1 and BRH2 are not erased even though the power supply to the electronic control unit 20 is shut off at the time of the engine stop, and used at the next engine start up time. If it is determined NO in step 305, namely, if the conditions for learning are not met, step 307 is executed.

Figure 5:
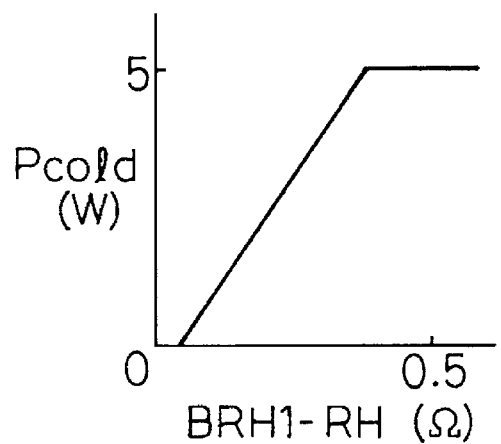
FIG. 5 is a characteristic graph showing a relationship between a value obtained by deducting the heater resistance RH from a learned value BRH1 and an amount of correction power energy $P_{cold}$.

In step 307, it is determined whether or not a condition for correcting the energy supplied to the air-fuel ratio sensor 15 during the warming up of the sensor 15 when it is cold (hereinafter it will be called the cold correction condition), is met. This is determined by confirming whether or not at least 10 minutes has passed after the engine started, for example, by executing another program not shown in FIG. 3. If it is determined that the cold correction condition is met, in step 308, the cold correction power energy $P_{cold}$ is calculated in accordance with a map, stored in ROM 22 shown in FIG. 5, based on difference between the first heater limit resistance BRH1 stored in the back-up RAM 27 and the current heater resistance RH obtained in step 302. The relationship between a value deducting the heater resistance RH from a learned value BRH1 (BRH1-RH) and an amount of correcting power energy $P_{cold}$, stored in the map is illustrated in a graph shown in FIG. 5. If it is determined that the cold correction condition is not met, in step 309, the amount of correcting power energy $P_{cold}$ is set to 0.

As will be explained below, the amount of correcting power energy $P_{cold}$ is added to the basic power energy $P_B$, so that the sensor element 16 of the air-fuel ratio sensor 15 in cold state can be quickly heated just after the engine started up, thereby accelerating the activation of the sensor element 16. The amount of correcting power energy $P_{cold}$ is set larger value as the difference between the first heater limit resistance BRH1 and the current heater resistance RH (BRH1-RH) increases, so that the power supply to the heater 17 increases as the heater resistance RH decreases, in other words, as the heater temperature decreases, the sensor element 16 can be quickly heated up. Furthermore, the amount of correcting power energy $P_{cold}$ is set to a small value or 0 when the difference (BRH1-RH) is small, so that excess power supply to the heater 17 can surely be avoided.

After the steps 308 or 309 have been executed, in step 310, it is determined whether or not another condition for correcting power supply to the air-fuel ratio sensor 15 when the sensor 15 is cold, because the engine is in the start up condition (hereinafter the start up correction condition), is true. This is determined by confirming whether or not at least 3 minutes has passed after the vehicle speed is increased from 0 km/h to over 0 km/h. This determination is performed by executing another program not shown in FIG. 3.

Figure 6:
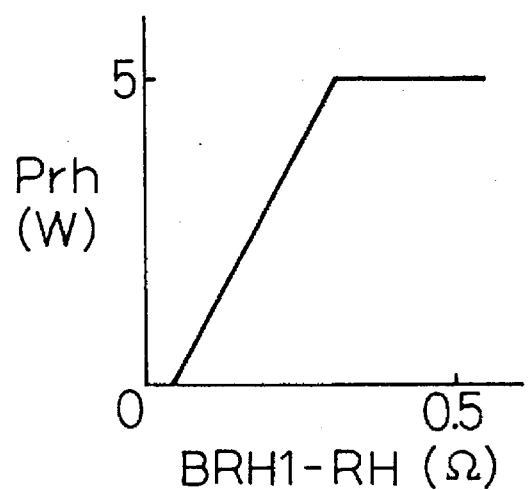
FIG. 6 is a characteristic graph showing a relationship between a value obtained by deducting the heater resistance RH from a learned value BRH1 and an amount of correction power energy $P_{rh}$.

If it is determined that the start up correction condition is met in step 311, the start up correction power energy $P_{rh}$ is calculated in accordance with a map, stored in ROM 22, shown in FIG. 6, based on difference between the first heater limit resistance BRH1 stored in the back-up RAM 27 and the current heater resistance RH obtained in step 302. The start up correction power energy $P_{rh}$ is equal to the power energy required to increase the temperature of the heater 17 until the heater resistance reaches the first heater limit resistance BRH1 from the current resistance RH. The relationship between a value obtained by deducting a learned value BRH1 from the heater resistance RH (RH-BRH1) and an amount of correction power energy $P_{rh}$, stored in the map is like the characteristic graph shown in FIG. 6. If it is determined that the start up correction condition is not met, in step 312, the amount of correction power energy $P_{rh}$ is set to 0.

As will be explained below, the amount of correction power energy $P_{rh}$ is added to the basic power energy $P_B$ for a period after the vehicle is started, so that the sensor element 16 of the air-fuel ratio sensor 15 may avoid being cooled down because the basic power energy $P_B$ for the heater 17 is decreased as the engine speed NE and the intake air pressure PM increase although the exhaust manifold 14 having the air-fuel ratio sensor 15 therein and the exhaust gas from the engine are not warm for a period after the vehicle started from its idling state.

In step 310, the start up correction condition is determined based on the vehicle speed. However, it can also be determined whether or not three minutes has passed since the engine speed NE become larger than the predetermined RPM or the throttle switch 19 is turned off.

After the steps 311 or 312 has been executed, in step 313, it is determined whether or not another condition for correcting power energy to the air-fuel ratio sensor 15 (hereinafter the OT correction condition), is true. This is performed by executing a flowchart shown in FIG. 8.

Figure 8:
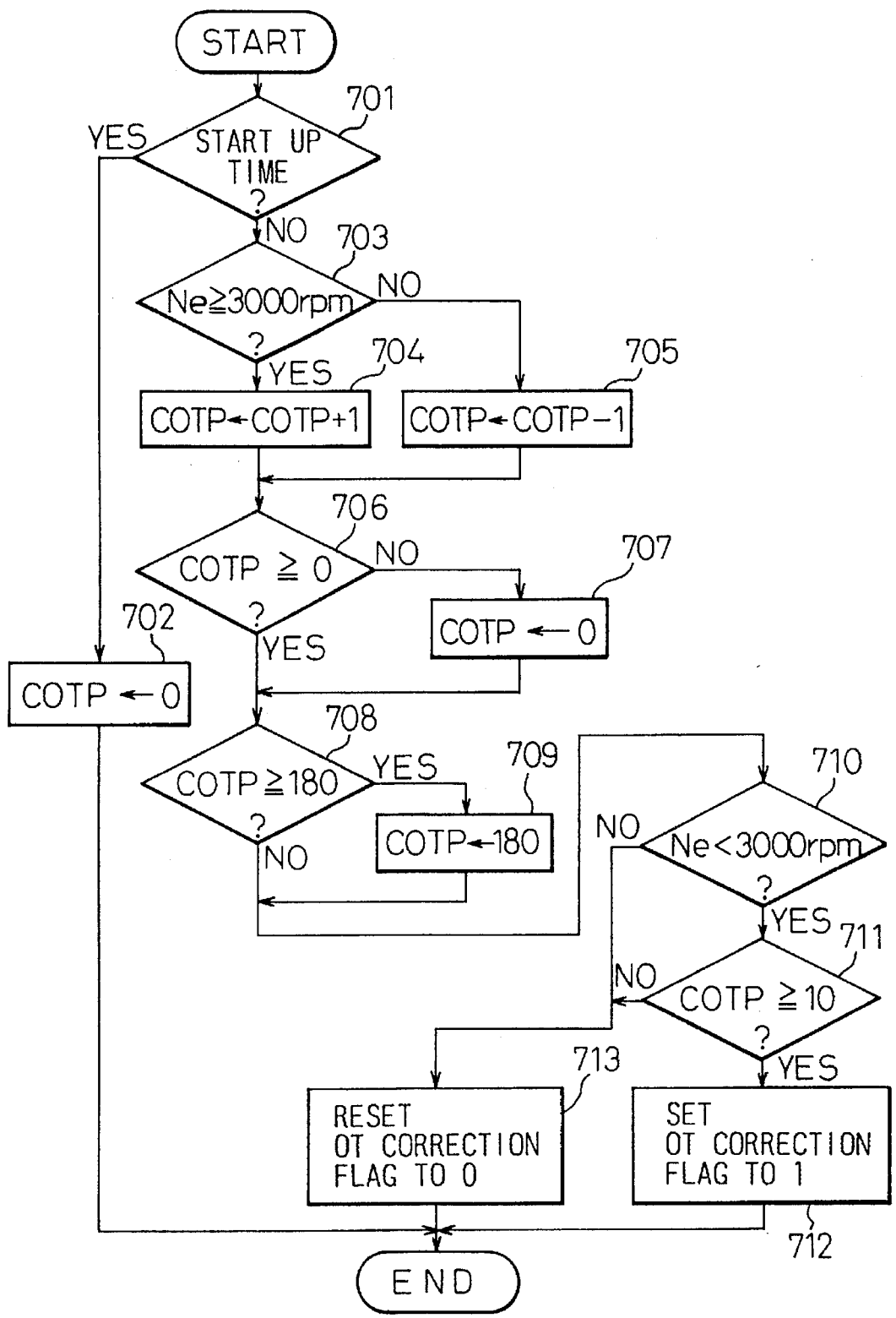
FIG. 8 is a flowchart showing a routine for determining whether or not conditions of an OT correction are met.

FIG. 8 is a flowchart showing a process for determining whether or not the conditions for the OT correction are true. This routine is executed by an interrupt that occurs at every predetermined time, for example, 1 sec. In step 701, it is determined whether or not the engine is currently in a start-up time. If the answer is YES, in step 702, a counter COTP is reset to 0, and the cycle ends.

If the answer is NO, in step 703, it is determined whether or not the current engine speed NE is equal to or greater than 3000 rpm. If NE≧3000 rpm, in step 704, the counter COTP is incremented by one, if NE<3000 rpm, in step 705, the counter COTP is decremented by one. After step 704 or 705 is executed, the cycle proceeds to step 706. And, in step 706, it is determined whether or not the counter COTP is COTP≧0. If COTP<0, in step 707, the counter COTP is reset to 0, if COTP≧0 or after step 707 is executed, in step 708, it is determined whether or not the counter COTP is COTP≧180. If COTP≧180, in step 709, the counter COTP is set to 180, if COTP<180 or after step 707 is executed, the cycle proceeds to step 710.

In step 710, it is determined whether or not the NE, if NE<3000 rpm. In step 711, it is determined whether or not the counter COTP is COTP≧10, and if COTP≧10, the cycle proceeds to step 712. If NE≧3000 rpm in step 711 or COTP<10 in step 711, the cycle proceeds to step 713. In step 712, a flag stored in the RAM 23 is set to 1 which indicates that the conditions of the OT correction are met, and the cycle ends. In step 713, the flag stored in the RAM 23 is reset to 0 because the conditions of the OT correction are not met, and the cycle ends. When the flag is set to 1, the sensor element 16 is in an active state.

As explained above, whether or not the conditions of the OT correction are met is determined by monitoring the value of the counter COTP. That is, it is considered that the conditions are met as long as the counter COTP, which is incremented when the engine speed NE is NE≧3000 rpm, is equal to or greater than 10 after the engine speed NE is decreased below 3000 rpm.

Figure 7:
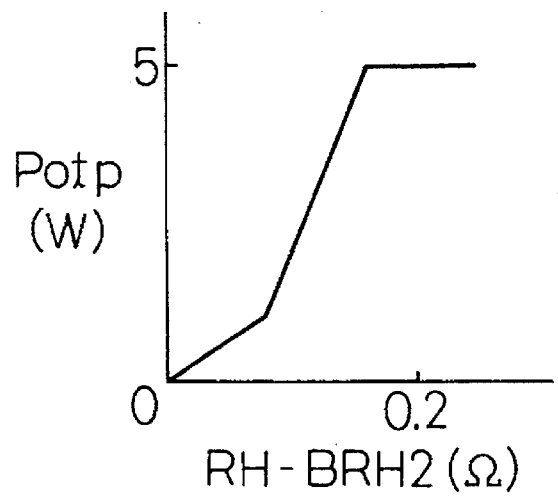
FIG. 7 is a characteristic graph showing a relationship between a value deducting the heater resistance RH from a learned value BRH1 and an amount of correction power energy $P_{ofp}$.

Returning to FIG. 3 again, in step 313, if it is determined that the OT correction conditions are met, the cycle proceeds to step 314. In step 314, the OT correction power energy $P_{ofp}$ is calculated in accordance with a map, stored in ROM 22 and shown in FIG. 7, based on difference between the second heater limit resistance BRH2 learned and stored in the back-up RAM 27 and the current heater resistance RH obtained in step 302. This OT correction power energy $P_{ofp}$ is equal to the power energy required to decrease the temperature of the heater 17 until the heater resistance reaches to the second heater limit resistance BRH2 from the current resistance RH. The relationship between a value obtained by deducting a learned value BRH2 from the heater resistance RH (RH-BRH2) and the amount of correction power energy $P_{ofp}$, stored in the map is like a characteristic graph shown in FIG. 7. If it is determined that the OT correction conditions are not met in step 313, the cycle proceeds to step 315, and sets the amount of OT correction power energy to $P_{ofp}$ which reduces the basic power energy $P_B$, to 0.

As will be explained below, the amount of OT correction power energy $P_{ofp}$ is deducted from the basic power energy $P_B$ for a period after the vehicle is driven in high speed, so that the sensor element 16 of the air-fuel ratio sensor 15 may avoid being overheated. Because, the basic power energy $P_B$ for the heater 17 is too much to keep the heater temperature in normal state due to the high temperature of the exhaust gas from the engine for the period after the vehicle is driven in high speed.

After executing steps 314 or 315, the cycle proceeds to step 316. In step 316, the full power energy $P_A$ is calculated based on the heater voltage $V_h$ and the current $I_h$ that are read in step 301. The power energy $P_A$ is equal to that continually supplied to the heater 17 for 100 msec, which means the power energy when the duty ratio is 100%.

Figure 9:
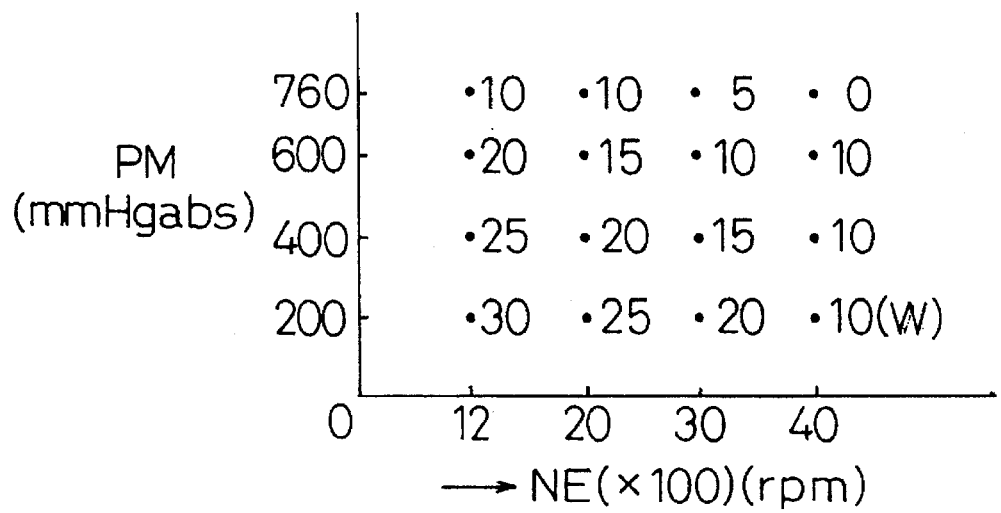
FIG. 9 is a map showing a routine for calculating a basic power energy.

In step 317, the basic power energy $P_B$ is calculated based on the engine speed NE and the intake air pressure PM that are read in step 301, for example, referring to the map shown in FIG. 9, which is stored in the ROM 22, then the cycle proceeds to step 318. As can be seen from the map shown in FIG. 9, the basic power energy $P_B$ is set low as the engine speed NE or the intake air pressure increases because the sensor element 16 can be heated by the warm exhaust gas from the engine that has burned more injected fuel. On the contrary, the basic power energy $P_B$ is set high as the engine speed NE or the intake air pressure decreases because the sensor element 16 cannot be heated with the exhaust gas from the engine that has burned less injected fuel.

In step 318, the target power energy $P_C$, i.e., the actual power energy, is calculated from the cold correction power energy $P_{cold}$, the start up correction power energy $P_{rh}$, the OT correction power energy $P_{ofp}$ and the basic power energy $P_B$ that are obtained in step 308, 311, 314 and 317 respectively as follows:

$$P_C = P_B + P_{cold} + P_{rh} - P_{ofp}$$

In step 319, the duty ratio D is calculated from the target power energy $P_C$ and the full power energy $P_A$ obtained in step 316 as follows:

$$D = (P_C/P_A) \times 100$$

Figure 10:
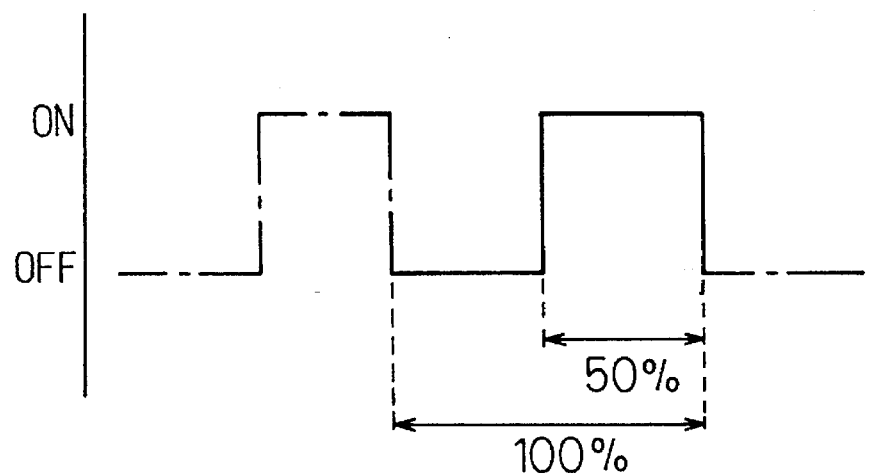
FIG. 10 is a timechart for explaining a control signal input to a heater current control circuit.

Then, in step 320, the pulse control signal according to the duty ratio obtained in step 319 is input to the heater current control circuit 33, thereby the power supply to the heater 17 is controlled, and the cycle ends. A pulse control signal of which the duty ratio is 50%, in which, for example, the full power energy $P_A$ is 50 (w·100 msec) and the target power energy $P_C$ is 25 (w·100 msec) is shown in FIG. 10, is input to the heater current control circuit 33.

As heretofore explained, the controller for a heater of an air-fuel ratio sensor, and the method for heating the air-fuel ratio sensor using a heater according to the present invention, the heater is controlled under a high temperature corresponding to a first heater limit resistance when the air-fuel ratio sensor has not yet warmed up at the engine start up time. Thus, the air-fuel ratio sensor can be rapidly activated and the air-fuel ratio feedback control of the engine for keeping the ratio at a target ratio, can be started in the early stage to clean the exhaust gas.

According to the controller and the method of the present invention, the heater is controlled under a temperature corresponding to a second heater limit resistance that is lower than the first upper limit after the air-fuel ratio sensor is warmed up because the air-fuel ratio sensor is kept activated. Thus, the air-fuel ratio sensor can be protected from overheating when the engine condition is changed from the heavy load to light load after the engine is warmed up, even if the temperature of the air-fuel ratio sensor and the surroundings of the sensor are increased by the exhaust gas and radiant heat from the engine body. In this way, the heater and the sensor element can avoid being deteriorated, and the efficiency of the power supply is improved.

It will be understood by those skilled in the art that the foregoing description is a preferred embodiment of the disclosed device and that various changes and modifications may be made in the invention without departing from the spirit and scope thereof.

I claim:

1. A controller for a heater of an air-fuel ratio sensor arranged in an exhaust gas system of an engine, the heater maintaining the air-fuel ratio sensor in an activated state, the controller comprising:

a power supplying device for supplying an amount of electric power to the heater as a function of a basic supply power amount which depends on engine operating conditions, the heater provided in the air-fuel ratio sensor;

a resistance measuring device for measuring a resistance of the heater; and a power supply controlling device controlling the an amount of electric power supplied to the heater by the power supplying device such that the resistance of the heater is maintained below a first upper limit while the air-fuel ratio sensor is being switched from a deactivated state to the activated state, the resistance of the heater being maintained below a second upper limit that is lower than the first upper limit after the air-fuel ratio sensor has reached the activated state by supplying an amount of electric power to the heater that is lower than the basic supply power amount, thereby avoiding deterioration of the heater and the air-fuel ratio sensor.

2. A method for controlling a heater of an air-fuel ratio sensor arranged in an exhaust gas system of an engine to maintain the air-fuel ratio sensor in an activated state while avoiding a deterioration of the heater and the air-fuel ratio sensor, comprising the steps of:

measuring a resistance of the heater;

controlling an amount of electric power provided to the heater as a function of a basic supply power amount which depends on engine operating conditions so that the measured resistance is maintained below a first upper limit when the air-fuel ratio sensor is switched from a deactivated state to the activated state; and controlling an amount of electric power provided to the heater so that the measured resistance is maintained below a second upper limit that is lower than the first upper limit by supplying an amount of electric power to the heater that is lower than the basic supply power amount after the air-fuel ratio sensor reaches the activated state.

* * * * *